US00PP26781P2

(12) United States Plant Patent
Kientzler

(10) Patent No.: US PP26,781 P2
(45) Date of Patent: May 31, 2016

(54) **NEW GUINEA *IMPATIENS* PLANT NAMED 'KIRORUF237'**

(50) Latin Name: *Impatiens hawkeri*
Varietal Denomination: Kiroruf237

(71) Applicant: Ludwig Kientzler, Gensingen (DE)

(72) Inventor: Ludwig Kientzler, Gensingen (DE)

(73) Assignee: Visioplant, Alajuela (CR)

( * ) Notice: Subject to any disclaimer, the term of this patent is extended or adjusted under 35 U.S.C. 154(b) by 4 days.

(21) Appl. No.: 14/121,724

(22) Filed: Oct. 11, 2014

(51) Int. Cl.
*A01H 5/02* (2006.01)

(52) U.S. Cl.
USPC ..... Plt./318.6

(58) Field of Classification Search
USPC ..... Plt./318.6
CPC ..... A01H 5/0261
See application file for complete search history.

*Primary Examiner* — Kent L Bell
(74) *Attorney, Agent, or Firm* — C. A. Whealy

(57) ABSTRACT

A new and distinct cultivar of New Guinea *Impatiens* plant named 'Kiroruf237', characterized by its compact, upright and mounded plant habit; freely branching habit; dense and bushy growth habit; dark green-colored leaves; and numerous bright lavender-colored flowers with undulate margins and positioned above and beyond the foliar plane.

1 Drawing Sheet

Botanical designation: *Impatiens hawkeri.*
Cultivar denomination: 'KIRORUF237'.

BACKGROUND OF THE INVENTION

The present invention relates to a new and distinct cultivar of New Guinea *Impatiens* plant, botanically known as *Impatiens hawkeri,* and hereinafter referred to by the name 'Kiroruf237'.

The new *Impatiens* plant is a product of a planned breeding program conducted by the Inventor in Gensingen, Germany. The objective of the breeding program was to develop new compact and freely branching *Impatiens* plants with numerous flowers and attractive leaf and flower colors.

The new *Impatiens* plant originated from a cross-pollination made by the Inventor in November, 2010, of a proprietary selection of *Impatiens hawkeri* identified as code number 09-311, not patented, as the female, or seed, parent with a proprietary selection of the *Impatiens hawkeri* identified as code number 09-175, not patented, as the male, or pollen, parent. The new *Impatiens* plant was discovered and selected by the Inventor as a flowering plant within the progeny of the stated cross-pollination in a controlled greenhouse environment in Gensingen, Germany in April, 2011.

Asexual reproduction of the new *Impatiens* plant by terminal cuttings propagated in a controlled greenhouse environment in Gensingen, Germany since May, 2011 has shown that the unique features of this new *Impatiens* plant are stable and reproduced true to type in successive generations of asexual reproduction.

SUMMARY OF THE INVENTION

Plants of the new *Impatiens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Kiroruf237'. These characteristics in combination distinguish 'Kiroruf237' as a new and distinct *Impatiens* plant:

1. Compact, upright and mounded plant habit.
2. Freely branching habit; dense and bushy growth habit.
3. Dark green-colored leaves.
4. Numerous bright lavender-colored flowers with undulate margins and positioned above and beyond the foliar plane.

Plants of the new *Impatiens* differ primarily from plants of the female parent selection in plant habit as plants of the new *Impatiens* are more compact than plants of the female parent selection.

Plants of the new *Impatiens* differ primarily from plants of the male parent selection in plant habit as plants of the new *Impatiens* are not as upright as plants of the male parent selection. In addition, plants of the new *Impatiens* are more freely branching than plants of the male parent selection.

Plants of the new *Impatiens* can be compared to plants of New Guinea *Impatiens* 'Vinflavimp', disclosed in U.S. Plant Pat. No. 23,222. In side-by-side comparisons conducted in Gensingen, Germany, plants of the new *Impatiens* differed primarily from plants of 'Vinflavimp' in the following characteristics:

1. Leaves of plants of the new *Impatiens* were darker in color than leaves of plants of 'Vinflavimp'.
2. Flower petals of plants of the new *Impatiens* had undulate margins whereas flower petals of plants of 'Vinflavimp' did not have undulate margins.
3. Plants of the new *Impatiens* and 'Vinflavimp' differed in flower color as plants of 'Vinflavimp' had light red purple-colored flowers with white-colored centers.

Plants of the new *Impatiens* can be compared to plants of New Guinea *Impatiens* 'Visinfblla', disclosed in U.S. Plant Pat. No. 16,147. In side-by-side comparisons conducted in Gensingen, Germany, plants of the new *Impatiens* differed primarily from plants of 'Visinfblla' in the following characteristics:

1. Flower petals of plants of the new *Impatiens* had undulate margins whereas flower petals of plants of 'Visinfblla' did not have undulate margins.
2. Plants of the new *Impatiens* and 'Visinfblla' differed in flower color as plants of 'Visinfblla' had purple and red bi-colored flowers.

BRIEF DESCRIPTION OF THE PHOTOGRAPHS

The accompanying photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet comprises a side perspective view of a typical flowering plant of 'Kiroruf237' grown in a container.

The photograph at the top of the sheet is a close-up view of a typical flowering plant of 'Kiroruf237'.

DETAILED BOTANICAL DESCRIPTION

The aforementioned photographs and following observations and measurements describe plants grown in Bonsall, Calif. during the summer in 11.5-cm containers in a polypropylene-covered shadehouse and under cultural practices typical of commercial New Guinea *Impatiens* production. During the production of the plants, day temperatures ranged from 24° C. to 27° C., night temperatures averaged 18° C. and light levels ranged from 2,500 to 4,000 foot-candles. Measurements and numerical values represent averages for typical flowering plants which were pinched one time and had been growing for four weeks after planting rooted young plants when the photographs and detailed description were taken. In the following description, color references are made to The Royal Horticultural Society Colour Chart, 2007 Edition, except where general terms of ordinary dictionary significance are used.

Botanical classification: *Impatiens hawkeri* 'Kiroruf237'.

Parentage:

*Female, or seed, parent*.—Proprietary selection of *Impatiens hawkeri* identified as code number 09-311 not patented.

*Male, or pollen parent*.—Proprietary selection of *Impatiens hawkeri* identified as code number 09-175, not patented.

Propagation:

*Type*.—Vegetative cuttings.

*Time to initiate roots, summer*.—About 14 days at temperatures about 20° C. to 22° C.

*Time to initiate roots, winter*.—About 18 days at temperatures about 19° C. to 21° C.

*Time to produce a rooted young plant, summer*.—About 18 days at temperatures about 20° C. to 22° C.

*Time to produce a rooted young plant, winter*.—About 21 days at temperatures about 19° C. to 21° C.

*Root description*.—Fibrous, medium in thickness; white in color.

*Rooting habit*.—Freely branching; medium density.

Plant description:

*Plant habit*.—Compact, upright and mounded plant habit.

*Growth and branching habit*.—Rapid growth rate; vigorous and freely branching habit; about six lateral branches developing at the base; dense and bushy growth habit; pinching, that is, removal of the terminal apices, is typically not required, but will enhance branching.

*Plant height*.—About 16.8 cm.

*Plant diameter or spread*.—About 29 cm.

*Lateral branches*.—Length: About 16 cm. Diameter: About 7 mm. Internode length: About 5.5 cm. Texture: Smooth, glabrous. Color: Close to 187A.

Leaf description:

*Arrangement*.—Opposite or in whorls, simple.

*Length*.—About 9.8 cm.

*Width*.—About 3.7 cm.

*Shape*.—Elliptical.

*Apex*.—Acuminate.

*Base*.—Attenuate.

*Margin*.—Serrulate with ciliation.

*Texture, upper and lower surfaces*.—Smooth, glabrous.

*Venation pattern*.—Pinnate.

*Color*.—Developing leaves, upper surface: Close to 139A. Developing leaves, lower surface: Close to 183B. Fully expanded leaves, upper surface: Close to 139A; venation, close to 187C. Fully expanded leaves, lower surface: Close to 183B; venation, close to 187B.

*Petioles*.—Length: About 1.8 cm. Diameter: About 4 mm. Texture, upper and lower surfaces: Smooth, glabrous. Color, upper and lower surfaces: Close to 183C.

Flower description:

*Flower type and flowering habit*.—Single axillary flowers; freely flowering habit with usually about six flowers and flower buds per lateral branch; flowers positioned above and beyond the foliar plane and typically face upright and outwardly.

*Flower longevity*.—Flowers last about one week under greenhouse conditions; petals self-cleaning, gynoecium persistent.

*Fragrance*.—None detected.

*Natural flowering season*.—Year-round under greenhouse conditions; in the garden, flowering from spring until fall in California; plants begin flowering about four weeks after planting young plants.

*Flower size*.—Diameter: About 4.5 cm by 5 cm. Depth: About 2.8 cm.

*Flower buds*.—Length: About 2.7 cm. Diameter: About 1.5 cm. Shape: Ovoid. Color: Close to N78C to N78D.

*Petals*.—Quantity and arrangement: Five petals arranged in a single whorl. Length, banner petal: About 2.4 cm. Length, lateral petals: About 2.7 cm. Length, lower petals: About 3 cm. Width, banner petal: About 4 cm. Width, lateral petals: About 3 cm. Width, lower petals: About 2.8 cm. Shape: Cordate. Apex: Emarginate. Base: Attenuate. Margin: Entire with irregular sinuate edges; undulate. Texture, upper and lower surfaces: Smooth, glabrous; velvety. Color: When opening, upper surface: Close to N78B. When opening, lower surface: Close to N74C. Fully opened, upper surface: Center, close to N78C; towards the apex, close to N78A; central longitudinal line, close to N78B; towards the base, close to 53A; colors do not fade with development. Fully opened, lower surface: Close to N78D.

*Sepals*.—Quantity and arrangement: Three arranged in a single whorl; one modified into an elongated spur.

Length: About 7 mm. Width: About 5 mm. Shape: Elliptical. Apex: Acuminate. Base: Obtuse. Margin: Entire. Texture, upper and lower surfaces: Smooth, glabrous. Color, upper and lower surfaces: Close to 53B. Spur length: About 4.2 cm. Spur diameter: At flower, about 2 mm; at apex, less than 1 mm. Spur texture: Smooth, glabrous. Spur color: Close to 53B.

*Peduncles*.—Length: About 3.1 cm. Diameter: About 2 mm. Angle: About 35° to 45° from vertical. Strength: Strong. Texture: Smooth, glabrous. Color: Close to 185A.

*Reproductive organs*.—Stamens: Quantity: Five fused at anthers; filaments free. Anther size: About 3 mm by 5 mm. Anther color: Close to 53A. Pollen amount: Moderate. Pollen color: Close to 158C. Pistils: Quantity per flower: One. Pistil length: About 6 mm. Stigma shape: Round. Stigma color: Close to 53D. Style color: Close to 53D. Ovary color: Close to 153A.

*Seeds and fruit*.—Seed and fruit development have not been observed on plants of the new *Impatiens*.

Disease & pest resistance: Plants of the new *Impatiens* have not been observed to be resistant to pathogens and pests common to New Guinea *Impatiens* plants.

Temperature tolerance: Plants of the new *Impatiens* have been observed to tolerate temperatures from about 16° C. to about 35° C.

It is claimed:

1. A new and distinct New Guinea *Impatiens* plant named 'Kiroruf237' as illustrated and described.

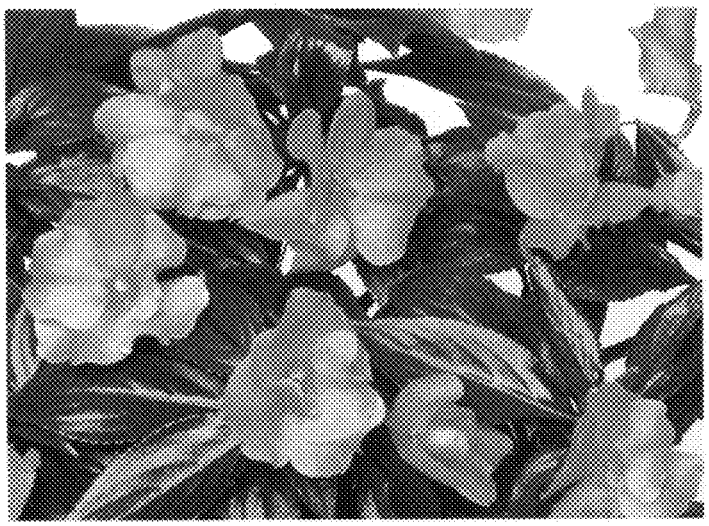
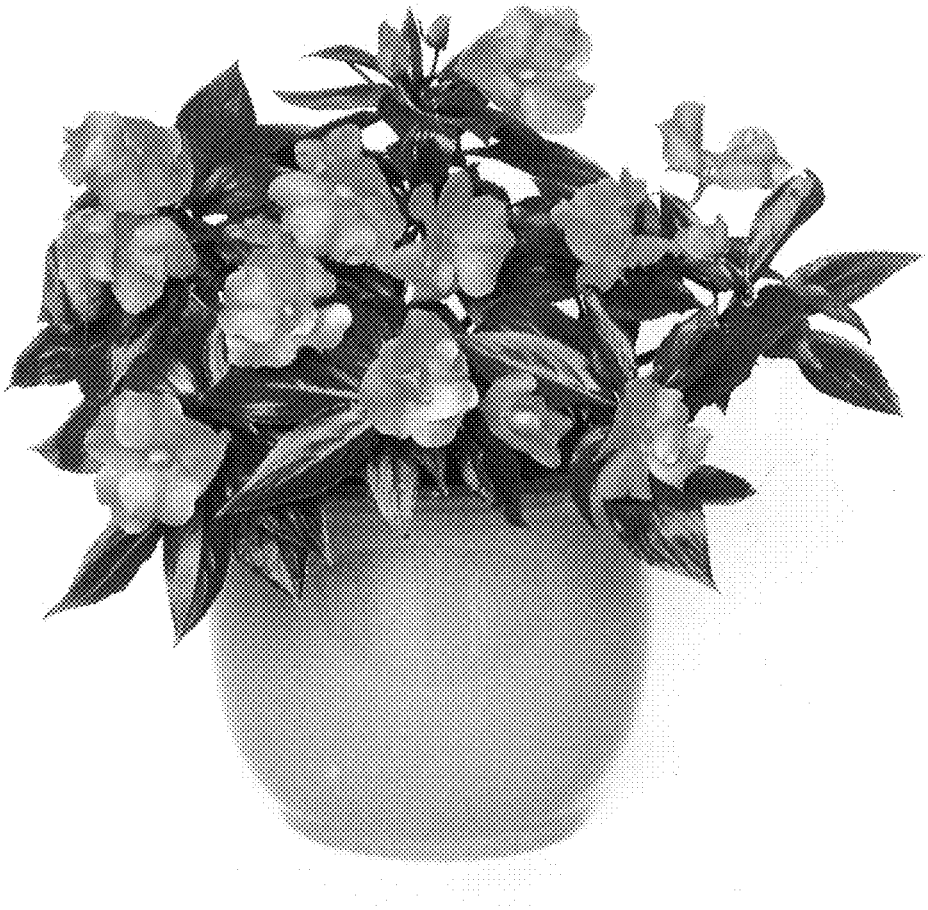

* * * * *